United States Patent [19]
Cai

[11] Patent Number: 5,851,369
[45] Date of Patent: Dec. 22, 1998

[54] ELECTROLYTIC SENSOR PROVIDING CONTROLLED BURN-OFF OF DEPOSITS ON THE ELECTRODES

[75] Inventor: Xiang Cai, Cincinnati, Ohio

[73] Assignee: Marathon Monitors, Inc., Cincinnati, Ohio

[21] Appl. No.: 716,998

[22] Filed: Sep. 20, 1996

[51] Int. Cl.$^6$ .................................................. G01N 27/407
[52] U.S. Cl. ........................ 204/428; 204/427; 205/784; 205/784.5
[58] Field of Search ..................................... 204/421–429

[56] References Cited

U.S. PATENT DOCUMENTS

| | | |
|---|---|---|
| 3,454,486 | 7/1969 | Davies . |
| 3,464,008 | 8/1969 | Meysson et al. . |
| 3,546,086 | 12/1970 | Sayles . |
| 3,597,345 | 8/1971 | Hickam et al. . |
| 3,616,407 | 10/1971 | Stuttgart . |
| 3,619,381 | 11/1971 | Fitterer . |
| 3,645,875 | 2/1972 | Record et al. . |
| 3,698,384 | 10/1972 | Jones . |
| 3,723,279 | 3/1973 | Fruehan et al. . |
| 3,981,785 | 9/1976 | Sandler . |
| 4,046,661 | 9/1977 | Stringer et al. . |
| 4,088,543 | 5/1978 | Ruka .......................................... 204/428 |
| 4,101,404 | 7/1978 | Blumenthal et al. . |
| 4,186,072 | 1/1980 | Blumenthal et al. . |
| 4,193,857 | 3/1980 | Bannister et al. . |
| 4,283,703 | 8/1981 | Horwitt . |
| 4,290,586 | 9/1981 | Kane et al. . |
| 4,319,966 | 3/1982 | Carlson et al. . |
| 4,356,065 | 10/1982 | Dietz . |
| 4,466,880 | 8/1984 | Torii et al. . |
| 4,588,493 | 5/1986 | Blumenthal et al. . |
| 4,647,364 | 3/1987 | Mase et al. . |
| 4,784,728 | 11/1988 | Capone ...................................... 204/428 |
| 4,786,374 | 11/1988 | Worrell et al. . |
| 4,814,061 | 3/1989 | Blumenthal et al. . |

FOREIGN PATENT DOCUMENTS

| | | |
|---|---|---|
| 1511066 | 12/1966 | France . |
| 2035882 | 2/1971 | Germany . |
| 2042249 | 3/1971 | Germany . |
| 2304075 | 8/1974 | Germany . |
| 2401134 | 8/1974 | Germany . |
| 1191222 | 5/1970 | United Kingdom . |
| 1296995 | 11/1972 | United Kingdom . |
| 1442391 | 7/1976 | United Kingdom . |

*Primary Examiner*—T. Tung
*Attorney, Agent, or Firm*—Dinsmore & Shohl LLP

[57] ABSTRACT

A sensor having a working electrode, a solid electrolyte and a counter electrode forming an electrolytic cell within a protective casing is provided. The sensor is utilized for monitoring the concentration of a specific constituent within a sample fluid by measuring the electrical potential difference between the electrode exposed to the sample fluid, which is the working electrode, and the counter electrode, which is exposed to a reference fluid. A protective casing shields the electrolytic cell from the sample fluid and access to the working electrode is provided by sample fluid ports provided in the protective casing. To minimize the surface area of the working electrode exposed to the sample fluid, a restricter is placed in the channel defined by the protective casing and the working electrode. Additionally, a burn-off gas inlet port is provided to controllably supply burn-off gas to the working electrode surface to burn-off any residual film formed on the working electrode surface exposed to the sample fluid. Additionally, a control system is provided which can use the output from a potential measuring device to control the supply of burn-off gas to the working electrode surface.

30 Claims, 2 Drawing Sheets

ELECTROLYTIC SENSOR PROVIDING CONTROLLED BURN-OFF OF DEPOSITS ON THE ELECTRODES

TECHNICAL FIELD

The present invention relates to electrolytic sensors for determining the concentration of a constituent of a fluid stream; and, more particularly, to such sensors having a sensing zone of limited area whereby the amount of residual film which may be deposited thereon is reduced and burn-off of the residual film is facilitated.

BACKGROUND OF THE INVENTION

Electrolytic sensors utilizing a solid electrolyte for measuring the concentration of a specific fluid, for example oxygen, within a sample fluid are known. Sensors may be used to measure, for example, the amount of oxygen in a furnace or other combustion chamber. It is often desirable, if not necessary, to insure that there is sufficient oxygen present within a chamber for combustion to progress. In some environments, for example, a reducing atmosphere, it may be necessary to measure and maintain the oxygen concentration in the range of parts per billion. Sensors are also used to determine the presence and/or concentration of noxious gases in enclosed environments, for example, in an underground storage tank.

To ensure that a monitored sample fluid is representative of the fluid within the environment being monitored, sensors should be sufficiently elongated to avoid sampling stagnant fluid near the walls of the enclosure. Elongated probes having one or more sample fluid inlet ports at the distal end of the probe have been used to ensure that a representative fluid sample is monitored.

To clean and regenerate a sensor it can be removed from its service environment, disassembled and cleaned. This is a time consuming, labor intensive, and costly procedure. Additionally, a back up sensor must be available during the period the sensor is being cleaned or there will be periods where no fluid monitoring occurs.

Alternatively, methods for in-situ cleaning of contaminated surfaces of a sensor have been developed. In some environments, for example, in a combustion chamber, the sensor is subjected to a high temperature sample gas which has a low oxygen concentration. Thus, by supplying a burn-off gas to the surface of the sensor which has an oxygen concentration sufficient to support combustion, the residual film on the surface of the sensor can be ignited by the high temperature sample gas and/or sensor surfaces, and the residual film is burned off. While this burn-off procedure removes the residual film, it also requires filling the sensing area with an oxygen rich gas, and, following the burn-off procedure, the sensing area of the sensor is filled with the combustion gas produced during the burn-off procedure. Accurate monitoring of the sample gas can not continue until the oxygen rich burn-off gas and the combustion gases produced during the burn-off procedure are removed from the sensing area. As a result, burn-off procedures are typically slow and create extended periods of time when the sensing probe is incapable of monitoring the sample gas.

Thus, there has been a continuing need for accurate, relatively simple, and inexpensive sensors. Additionally, there is a need for a sensor which can be both easily cleaned of residual films on the sensing surfaces, and quickly and easily purged of the burn-off gas and the combustion gases produced during the burn-off procedure.

SUMMARY OF THE INVENTION

Accordingly, it is an object of the present invention to obviate problems of the prior art. It is a related object of the present invention to provide a sensor having an elongated protective casing wherein only a portion of the working electrode within the protective casing is exposed to a sample fluid.

It is an additional object of the present invention to controllably supply a burn-off gas to the surface of a working electrode exposed to a sample fluid.

Accordingly, the present invention, in one embodiment, comprises a sensor having a working electrode, a solid electrolyte and a counter electrode. The outer surface of the working electrode is exposed to a sample fluid, for example a gas, the inner surface of the working electrode is in contact with the outer surface of the solid electrolyte, while the inner surface of the solid electrolyte is in contact with an outer surface of the counter electrode. The inner surface of the counter electrode is in contact with a reference fluid, for example a reference gas.

An electrochemical potential difference between the working electrode and the counter electrode may develop and can be measured. A potential difference can occur if the concentration of the sample fluid in contact with the outer surface of the working electrode differs in concentration of the particular constituent being monitored, with respect to the reference fluid in contact with the inner surface of the counter electrode. The working electrode, solid electrode and counter electrode define an electrolytic cell which is housed within a protective casing. The protective casing is arranged in spaced relation to the working electrode defining a channel therebetween. The surface area of the working electrode exposed to the sample fluid is minimized through the use of a channel restricter which effectively blocks the sample fluid from entering a portion of the channel between the working electrode and the protective casing.

A burn-off gas inlet port, and more preferably, a burn-off gas inlet line in communication with the burn-off gas inlet port, is provided in the channel restricter. The burn-off gas inlet port allows a burn-off gas to be supplied to the sensing zone defined by the protective casing, the working electrode and the channel restricter. The burn-off gas, when supplied, can ignite a residual film on the surface of the working electrode.

The sensors of the present invention provide significant advantages over the prior art. The sensors described herein, which have an elongated protective casing for sampling fluids away from the effects of the surrounding walls, also have a limited sensing zone. The sensing zone is defined by a channel restricter within a channel defined by the outer surface of the working electrode and the inner surface of the protective casing. By limiting the sensing zone, the surface area of the working electrode exposed to the sample fluid is likewise limited. Thus, there is less surface area of the working electrode on which a residual film can build up. Subsequently, there is less residual film to burn-off during the burn-off procedure. Additionally, by limiting the sensing zone the amount of burn-off gas required to remove the residual film on the working electrode is reduced, which reduces the time for each burn-off sequence. Likewise, the time required for the combustion gases created during the burn-off sequence to be purged from the sensing zone is also reduced. Thus, the entire burn-off procedure is significantly reduced compared to sensors of the past.

BRIEF DESCRIPTION OF THE DRAWINGS

While the specification concludes with the claims particularly pointing out and distinctly claiming the present invention, it is believed that the same will better be understood from the following description taken in conjunction with the accompanying drawings in which:

DETAILED DESCRIPTION

Figure 1:
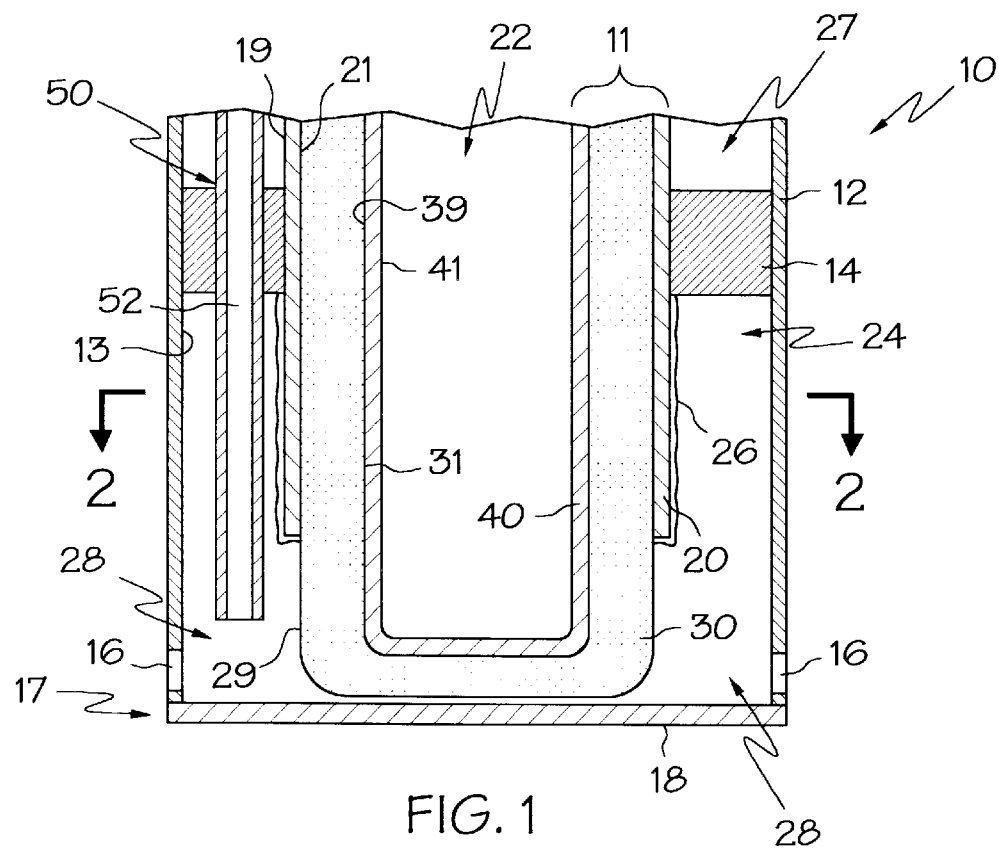
FIG. 1 is a partial cross-sectional schematic view of a cylindrical sensor of the present invention.

Referring now to the drawings in detail, wherein FIG. 1 is a partial schematic cross-sectional view of a cylindrical sensor of the present invention. While the sensors of the present invention are described in conjunction with a cylindrical embodiment, it is understood that other geometric configuration, for example, a substantially flat sensor, are appropriate for use with the present invention. Sensor 10 comprises an electrolytic cell 11 which comprises a working electrode 20, a solid electrolyte 30 and a counter electrode 40.

Figure 2:
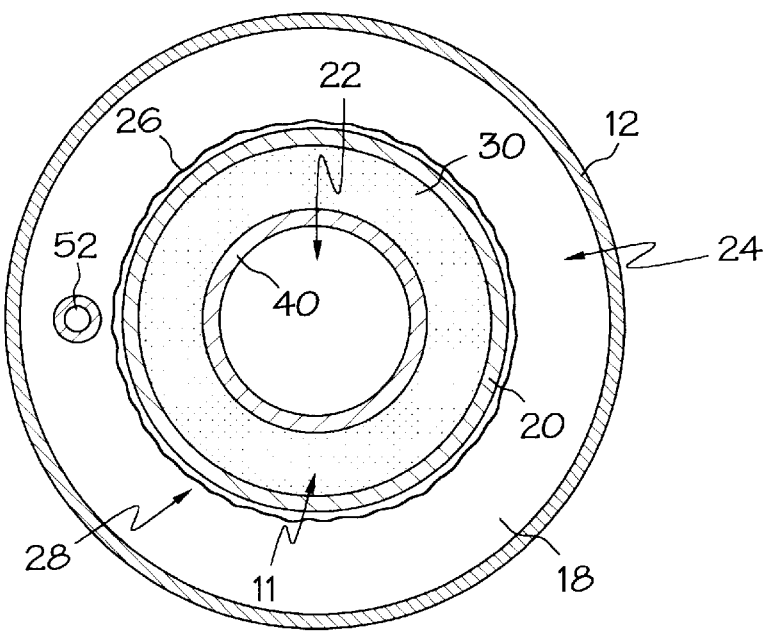
FIG. 2 is a schematic cross-sectional view of the cylindrical sensor of FIG. 1 taken along line 2—2.

Working electrode 20 has a working electrode outer surface 19 and working electrode inner surface 21. Solid electrolyte 30 has an electrolyte outer surface 29 which is in contact with working electrode inner surface 21 and a electrolyte inner surface 31. Counter electrode 40 has a counter electrode outer surface 39 which is in contact with electrolyte inner surface 31 and a counter electrode inner surface 41. In the preferred embodiment of the electrolytic cell 11 shown in FIGS. 1 and 2, the working electrode 20, solid electrolyte 30 and counter electrode 40 are all hollow cylinders which are arranged concentrically. Counter electrode inner surface 41 defines an interior cylindrical channel 22 which, during operation, is typically filled with a reference fluid. The reference fluid is typically air but can be any fluid which has a known concentration of the fluid constituent being monitored and which is compatible with counter electrode inner surface 41.

Electrolytic cell 11 is housed within a protective casing 12 having a protective casing inner surface 13. Protective casing inner surface 13 and working electrode outer surface 19 define an exterior annular channel 24. A casing cap 18 is preferably provided to enclose exterior annular channel 24.

Figure 3:
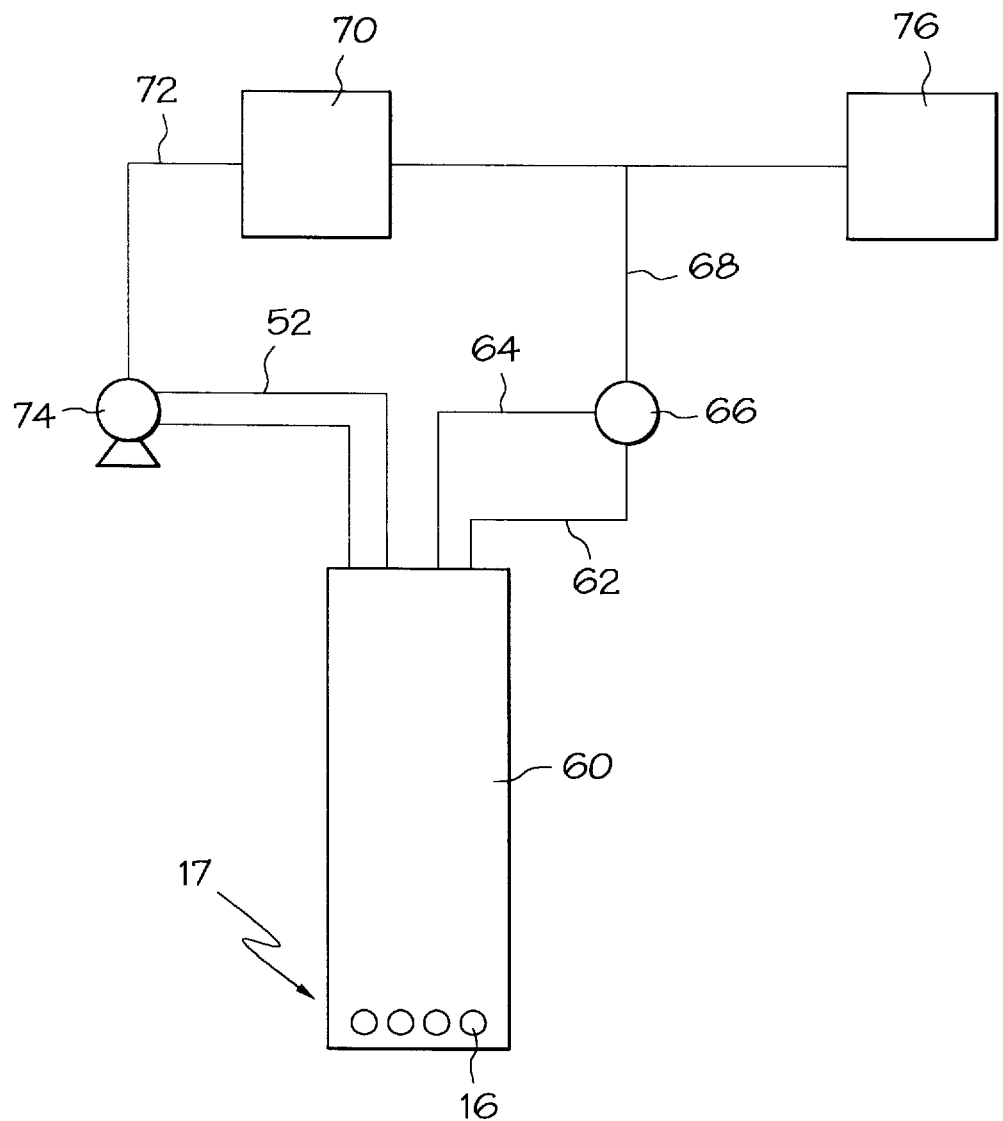
FIG. 3 is a schematic control diagram utilizing a sensor according to the present invention.

A sample fluid enters the exterior annular channel through fluid ports 16, which are provided in protective casing 12. Fluid ports 16 allow fluid to enter and exit exterior annular channel 24. Two fluid ports 16 are shown in FIG. 1, and a plurality of fluid ports 16 are shown on sensor 60 of FIG. 3. However, it is understood that only one fluid port 16 is necessary, although more than one may be preferred in certain instances. Fluid ports 16 can be of any appropriate geometric configuration and it is preferred that fluid ports 16 be adjacent protective casing distal end 17. Likewise, if provided, casing cap 18 is adjacent protective casing distal end 17.

Sensor 10 additionally comprises a channel restricter 14. Channel restricter 14 is secured within exterior annular channel 24 and defines a portion of channel 24 as a sensing zone 28 and a portion of channel 24 as a non-sensing zone 27. Restricter 14 can be secured by any appropriate means, for example sealants, or restricter 14 can be compressively secured between protective casing inner surface 13 on working electrode outer surface 19.

During operation of sensor 10, sample fluid entering sensing zone 28 can cause a residual film 26 to develop on working electrode outer surface 19. Residual film 26 can, and most likely will, effect the accuracy of electrolytic cell 11. Thus, it is desirable to "clean" working electrode outer surface 19 by at least partially removing residual film 26. Residual film 26 can be any foreign substance on the surface of the working electrode 20, whether caused by a physical deposit of particulate matter, the residue from a chemical reaction of the sample fluid with the working electrode outer surface 19, or deposited by any other means.

A burn-off gas inlet 50 is provided in channel restricter 14 for the purpose of supplying a burn-off gas to sensing zone 28. A burn-off gas inlet line 52 is preferably provided to supply burn-off gas to burn-off gas inlet 50. The burn-off gas supplied to sensing zone 28 is typically air, which has a concentration of oxygen of greater than about 20% by volume. Other burn-off gases, which have a sufficient concentration of oxygen to support combustion, can be used. It is preferred that the burn-off gas have at least about 12% oxygen by volume to insure adequate combustion and burn-off of residual film 26 formed on working electrode outer surface 19.

Burn-off gas inlet line 52 can be placed within non-sensing zone 27 to connect burn-off gas inlet 50 with a source of the burn-off gas. Alternatively, non-sensing zone 27 can be filled with a burn-off gas and burn-off gas inlet 50 provided with a controllable valve (not shown) to control the supply burn-off gas to the sensing zone 28. As can be appreciated, the pressure of the burn-off gas in non-sensing zone 27 will necessarily be greater than the pressure of sample fluid in the sensing zone 28 in order for burn-off gas to flow through burn-off gas inlet 50.

The sensors described herein are often used as gas sensors. More specifically, the gas sensors of the present invention can be used as oxygen sensors in a combustion chamber, for example an incinerator or gas furnace. Thus, it is preferred that all materials exposed to the sample gas be capable of withstanding temperatures of greater than about 1500° F., and more preferably, capable of withstanding temperatures of up to about 2000° F. In a combustion environment the sample gas typically has an oxygen concentration of less than about 12% by volume.

Working electrode 20 and counter electrode 40 can be made from a variety of materials including Nichrome Alloys, although platinum is preferred. Additionally, because electrochemical sensing is typically a surface phenomenon, coated electrodes can be used. For example, carbon electrodes coated with platinum, or any of the materials listed above, can be used.

The solid electrolyte 30 is preferably zirconia. The protective casing 12, and if supplied protective casing cap 18, should be formed of a heat resistant material. Alloys of Iron are acceptable for use as protective casing 12 and cap 18. Burn-off gas inlet line 52 can be any of a variety of heat resistant materials such as Alumina.

Channel restricter 14 is preferably an electrically non-conductive material, for example, a ceramic material or refractory material. Because channel restricter 14 may be in contact with working electrode 20 and may also be in contact with protective casing inner surface 13, it is preferred that if channel restricter 14 is an electrically conductive material that it be insulated from at least one of these surfaces, preferably working electrode 20. It is preferred that restricter 14 does not conduct current from working electrode 20, and it is especially preferred that current not be transmitted to protective casing 12.

As can be understood working electrode 20 can be either a cathode or an anode and counter electrode 40 can likewise be a cathode or an anode. As can be appreciated when working electrode 20 is a cathode counter electrode 40 is an anode, and when working electrode 20 is an anode counter electrode 40 is a cathode. When sensor 10 is utilized as an oxygen sensor, working electrode 20 is a cathode and counter electrode 40 is an anode. For gas sensors, the electrochemical reduction/oxidation potential of the gas constituent being monitored, and the reference gas within interior cylindrical channel 22, will determine whether the working electrode is a cathode or an anode. Thus, the nature of the electrolytic cell can change depending upon the particular gas constituent within the sample gas which is being monitored.

Having shown and described the preferred embodiments of the present invention, further adaptation of the sensors can be accomplished by appropriate modifications by one of ordinary skill in the art without departing from the scope of the present invention. A number of alternatives and modifications have been described herein and others will be apparent to those skilled in the art. For example, specific materials of construction for the sensors have been described, although other material can be used to produce the desired sensors. Also, the present invention has been described in conjunction with a cylindrical sensor having concentric electrodes but other geometric configurations, for example, flat and multi-sided sensors can be used with the present invention. Accordingly, the scope of the present invention should be considered in terms of the following claims and is understood not to be limited to the details of the products shown and described in the specifications.

I claim:

1. A sensor, comprising;
   a working electrode having an outer surface and an inner surface, a solid electrolyte having an outer surface and an inner surface, and a counter electrode having an outer surface and an inner surface, the inner surface of the working electrode being in contact with the outer surface of the solid electrolyte, the inner surface of the solid electrolyte being in contact with the outer surface of the counter electrode, and the inner surface of the counter electrode being exposed to a reference fluid;
   an elongated protective casing arranged in spaced relation to the outer surface of the working electrode and defining a channel therebetween, the casing comprising a sample fluid port which permits a sample fluid to enter the channel;
   a channel restrictor adjacent the sample fluid port, the channel restrictor defining a portion of the channel as a sensing zone and a portion of the channel as a non-sensing zone and reducing the volume of the channel which is exposed to the sample fluid;
   a burn-off gas inlet adapted to inject a burn-off gas into the sensing zone, and
   a burn-off gas in communication with the burn-off gas inlet, the burn-off gas having an oxygen concentration greater than an oxygen concentration in the sample fluid.

2. The sensor of claim 1, further comprising a plurality of sample fluid ports through which a sample fluid enters or exits the sensing zone of the channel.

3. The sensor of claim 2, wherein the protective casing has a distal end and the sample fluid ports and the sensing zone are adjacent the distal end of the casing.

4. The sensor of claim 3, further comprising a casing cap adjacent the distal end of the protective casing.

5. The sensor of claim 1, further comprising a burn-off gas line for supplying the burn-off gas to the burn-off gas inlet.

6. The sensor of claim 5, wherein the burn-off gas line is substantially housed within the non-sensing zone.

7. The sensor of claim 1, wherein the counter electrode and the working electrode are formed of platinum.

8. The sensor of claim 1, wherein the protective casing is formed of a Nichrome alloy.

9. The sensor of claim 1, wherein the sensor is a gas sensor.

10. The sensor of claim 1, wherein the sensor is an oxygen sensor.

11. The sensor of claim 1, wherein the counter electrode is an anode and the working electrode is a cathode.

12. The sensor of claim 1, wherein the counter electrode is a cathode and the working electrode is an anode.

13. The sensor of claim 1, wherein the solid electrolyte is formed of zirconia.

14. The sensor of claim 1, further comprising a programmable controller for controlling an amount of burn-off gas injected into the sensing zone, a period of time during which burn-off gas is injected into the sensing zone, and a time period in which injection of burn-off gas is interrupted.

15. The sensor of claim 1, further comprising a potentiometer for monitoring a difference in the electrical potential between the working electrode and the counter electrode.

16. A cylindrical sensor, comprising;
   a hollow cylindrical working electrode having an outer surface and an inner surface, a hollow cylindrical solid electrolyte having an outer surface and an inner surface, and a hollow cylindrical counter electrode having an outer surface and an inner surface, the inner surface of the working electrode being in contact with the outer surface of the solid electrolyte, the inner surface of the solid electrolyte being in contact with the outer surface of the counter electrode, and the inner surface of the counter electrode being exposed to a reference fluid;
   an elongated hollow cylindrical protective casing arranged in spaced relation to the outer surface of the working electrode and defining an annular channel therebetween, the casing comprising a sample fluid port which permits a sample fluid to enter the annular channel;
   an annular channel restricter adjacent the sample fluid port, the annular channel restricter defining a portion of the annular channel as an annular sensing zone and a portion of the channel as a non-sensing zone, and reducing the volume of the annular channel which is exposed to the sample fluid;
   a burn-off gas inlet adapted to inject a burn-off gas into the annular sensing zone, and
   a burn-off gas in communication with the burn-off gas inlet, the burn-off gas having an oxygen concentration greater than an oxygen concentration in the sample fluid.

17. The cylindrical sensor of claim 16, further comprising a plurality of sample fluid ports through which a sample fluid enters or exits the annular sensing zone of the annular channel.

18. The cylindrical sensor of claim 16, wherein the cylindrical protective casing has a distal end and the sample fluid ports and the annular sensing zone are adjacent the distal end of the casing.

19. The cylindrical sensor of claim 18, further comprising a casing cap adjacent the distal end of the protective casing.

20. The cylindrical sensor of claim 16, further comprising a burn-off gas line for supplying the burn-off gas to the burn-off gas inlet.

21. The cylindrical sensor of claim 20, wherein the burn-off gas line is substantially housed within the non-sensing zone.

22. The cylindrical sensor of claim 16, wherein the cylindrical counter electrode and the cylindrical working electrode are formed of platinum.

23. The cylindrical sensor of claim 16, wherein the cylindrical protective casing is formed of a Nichrome alloy.

24. The cylindrical sensor of claim 16, wherein the cylindrical sensor is a gas sensor.

25. The cylindrical sensor of claim 16, wherein the cylindrical sensor is an oxygen sensor.

26. The cylindrical sensor of claim 16, wherein the cylindrical counter electrode is an anode and the cylindrical working electrode is a cathode.

27. The cylindrical sensor of claim 16, wherein the cylindrical counter electrode is a cathode and the cylindrical working electrode is an anode.

28. The cylindrical sensor of claim 16, wherein the cylindrical solid electrolyte is formed of zirconia.

29. The cylindrical sensor of claim 16, further comprising a programmable controller for controlling an amount of burn-off gas injected into the annular sensing zone, a period of time during which burn-off gas is injected into the annular sensing zone, and a time period in which injection of burn-off gas is interrupted.

30. The cylindrical sensor of claim 16, further comprising a potentiometer for monitoring a difference in the electrical potential between the cylindrical working electrode and the cylindrical counter electrode.

* * * * *